United States Patent [19]
Hart et al.

[11] Patent Number: 5,848,992
[45] Date of Patent: Dec. 15, 1998

[54] SUPERFASCIAL SURGICAL ACCESS DEVICE

[76] Inventors: Charles C. Hart, 8252 Mandeville Dr., Huntington Beach, Calif. 92646; Eric Lee, 125 Osford, Irvine, Calif. 92612; Eduardo Chi-Sing, 75 Shorebreaker Dr., Laguna Niguel, Calif. 92677

[21] Appl. No.: 814,746

[22] Filed: Mar. 7, 1997

[51] Int. Cl.$^6$ .................................................. A61M 5/178
[52] U.S. Cl. ............................................................ 604/167
[58] Field of Search ................................... 604/167, 174, 604/175, 180; 128/DIG. 26

[56] References Cited

U.S. PATENT DOCUMENTS

| | | | |
|---|---|---|---|
| 2,898,917 | 8/1959 | Wallace | 128/350 |
| 4,519,793 | 5/1985 | Galindo | 604/180 |
| 4,578,063 | 3/1986 | Inman et al. | 604/175 |
| 4,593,681 | 6/1986 | Soni | 128/4 |
| 4,804,369 | 2/1989 | Lapeyre et al. | 604/175 |
| 4,809,679 | 3/1989 | Shimonaka et al. | 604/167 X |
| 5,073,169 | 12/1991 | Raiken | 604/180 |
| 5,137,520 | 8/1992 | Maxson et al. | 604/180 |
| 5,215,531 | 6/1993 | Maxson et al. | 604/180 |
| 5,263,939 | 11/1993 | Wortrich | 604/174 |
| 5,342,319 | 8/1994 | Watson et al. | 604/167 X |
| 5,352,211 | 10/1994 | Merskelly | 604/180 |
| 5,354,283 | 10/1994 | Bark et al. | 604/180 |
| 5,364,367 | 11/1994 | Banks et al. | 604/174 |
| 5,366,478 | 11/1994 | Brinkerhoff et al. | 660/213 |
| 5,375,588 | 12/1994 | Yoon | 128/4 |
| 5,496,280 | 3/1996 | Vandenbroek et al. | 604/167 |
| 5,514,133 | 5/1996 | Golub et al. | 604/175 X |
| 5,558,641 | 9/1996 | Glantz et al. | 604/175 X |
| 5,611,792 | 3/1997 | Gustafsson | 604/167 X |
| 5,662,616 | 9/1997 | Bousquet | 604/175 |

*Primary Examiner*—Wynn Wood Coggins
*Assistant Examiner*—Deborah Blyveis

[57] ABSTRACT

A surgical access device for providing gas tight communication to an anatomical cavity which facilitates the insertion and use of surgical instruments while maintaining the anatomical cavity. The access device allows for the use of laparoscopic instruments in tight surgical locations without the need for a trocar or other supportive device. In addition, the surgical access device allows the use of non-laparoscopic instruments in a laparoscopic setting to add flexibility and improved sterility to an open surgery. Increased surgical instrument access and mobility within the anatomical cavity is achieved with a reduced need for insufflation. The access surgical device includes a flexible planer base with an integral opening for isolating and maintaining an open surgical incision. A hollow stem having an instrument seal is attached to the base over the incision. The stem also includes a valve for maintaining a positive gas pressure within the anatomical cavity.

14 Claims, 4 Drawing Sheets

SUPERFASCIAL SURGICAL ACCESS DEVICE

FIELD OF THE INVENTION

This invention relates generally to surgical devices and more particularly, to a device and associated method for providing and maintaining sealed access into an anatomical cavity.

BACKGROUND OF THE INVENTION

Minimally invasive surgical methods and techniques are becoming more common for performing various types of surgical operations. Unlike other types of surgical procedures, these techniques generally don't require large incisions or body openings to expose the internal organs or other internal tissues within an operable region. Such techniques may include laparoscopic, endoscopic and similar types of surgeries. The advantage of these minimally invasive surgical techniques include, reduced trauma, reduced blood loss, minimal scarring, minimized infection and reduced recovery time.

In particular, laparoscopic surgery is a recently introduced, minimally invasive, surgical technique for performing various types of surgical operations within an operable region. The procedure typically begins by cutting a small hole through the body wall adjacent the desired operable region. A tubular sheath or cannula is inserted into the hole to create and maintain an access path with the operable region. A trocar which includes a cannula is generally used for this step. The operable region is then filled with a pressurized gas to create an anatomical cavity (inflated peritoneum) in order to safely manipulate surgical instruments within the desired body region. Surgical instruments may then be inserted through the trocar such that the laparoscopic surgery can be performed. A seal within the trocar prevents the loss of gas pressure and thus the anatomical cavity.

Laparoscopic techniques, like other similar minimally invasive surgical techniques are becoming widely accepted because of their many advantages. However, there are also some disadvantages. For example, there are limitations on the ability and freedom to manipulate organs and tissues using laparoscopic instruments. Another disadvantage occurs when a tissue specimen must be removed. This situation often requires a larger opening than the hole maintained by the trocar. Removing the trocar, increasing the opening size in the body wall or otherwise attempting to remove the tissue can cause a loss of the gas pressure in a distended anatomical cavity, including a collapse of the cavity wall, and loss of interior working and viewing space. A number of these and other disadvantages are directly attributable to the use of a trocar.

A typical trocar includes a housing, a cannula and a seal. The housing is generally superfascially mounted on the patient adjacent the operable region. The housing is connected to the cannula which provides the working channel into the operable region. The seal is mounted within the housing and maintains a positive gas pressure within the anatomical cavity. The seal also permits the passage of surgical instruments while minimizing the loss of gas pressure or sterility. Most laparoscopic or similar surgical procedures require the use of several trocars for insertion of various surgical instruments into a number of different locations within the operable cavity.

Trocars are typically made from either metal, a rigid plastic or a combination. Reusable or sterilizable trocars are made of stainless steel while the disposable or single use trocars are typically made of plastic. The seal portions of the trocars are normally made of an elastomeric material such as rubber or silicone. In most cases, the trocar is rigid and has a fixed length and a fixed diameter. In addition, existing trocars are not axially or radially flexible and the housing portion must remain superfascially fixed against the patient during the surgical procedure.

In certain laparoscopic procedures, there may be a need to access an operable region with a surgical instrument which is not possible while using a trocar. In these situations, there may not be sufficient space to accommodate a cannula. Such procedures may include surgeries close to the body surface as well as surgeries on the extremities. Other surgical procedures require the ability to manipulate and change the angle of the surgical instrument within the anatomical cavity to a degree not generally possible when using a rigid trocar. These surgeries may further include the need for access to the operable region by both laparoscopic instruments as well as for open surgery techniques. Thus, there is a need for a surgical access device which allows laparoscopic instrument access within an operable region and which retains many of the advantages of minimally invasive surgery without the need for a trocar or cannula. There is also a need for such an access device which provides for both laparoscopic as well as open surgery techniques.

In addition, there are also various laparoscopic and other surgical procedures that could benefit oblique or angular access. These procedures, which may include certain surgical maneuvers such as vein harvesting techniques, are not generally possible with a trocar which is rigid. Other procedures require the use of surgical instruments that are irregular in shape and which cannot fit through the rigid channel of a trocar cannula. Thus, there is a need for a surgical access device which allows angular access, including increased maneuverability and the ability to utilize irregularly shaped instruments without the need for a trocar.

One of the advantages of laparoscopic techniques is the ability to create an operable anatomical cavity by introducing and maintaining a gas pressure through the trocar and into the operable region. However, there are a variety of surgical procedures, both laparoscopic and non-laparoscopic which don't need or can't use a trocar but do require an inflated anatomical cavity within the operative region.

These procedures, which include open surgery techniques, often require the ability to provide instrument access to within the operable region as well as to maintain gas pressure within the anatomical cavity. In addition, these procedures which can't utilize a trocar could still benefit from the smaller incision generally required along with the many other advantages associated with trocars and minimally invasive surgery. In some surgical procedures, there may also be a need to create and maintain an open anatomical cavity without the use of a trocar and without using gas pressure. Thus, there is a need for a surgical access device which can create and maintain an anatomical cavity while providing access for surgical instruments without the need for a trocar.

There is therefore, the need for a surgical access device and technique which allows communication into an operable region while providing the benefits of laparoscopic surgery and some of the convenience and benefits of open surgery. There is also a need for such a device which does not require a trocar or other rigid housing and cannula members. There is also a need for such a device which can maintain a sterile environment during a surgical procedure and provide a flexible access for the manipulation of surgical instruments. There is also a need for such a device which is inexpensive to manufacture and simple to use.

SUMMARY

The present invention satisfies the need for a surgical access device which provides for many of the advantages of minimally invasive surgical techniques without the need for a trocar or a cannula. As a consequence, laparoscopic procedures may be utilized with the device of the present invention which would otherwise be impossible due to the lack of space for a trocar or a trocar-like device. The invention also enables the use of non-laparoscopic and irregularly shaped instruments in a laparoscopic setting, allowing a surgeon to switch back and forth between open surgery and laparoscopic surgery techniques.

The present invention also satisfies the need for a surgical access device which can be used to create and maintain an operable cavity within the body by providing an access device having both an instrument seal and an operative valve. Using a flexible base and hollow stem which incorporates the valve and seal, the invention allows increased maneuverability in both laparoscopic and open surgical instruments. In addition, the secure attachment of the base to the skin along with the flexible design of the hollow stem provides access for both laparoscopic and open surgical instruments without the need for a trocar.

Generally, and in broad terms, the surgical access device of the present invention is used to isolate and maintain a surgically made superfascial incision and for providing a sealed access path into an operable region in communication with the incision. In one embodiment, the surgical access device includes a flexible base which is removably attached to a portion of the skin adjacent the incision. The base includes an opening for isolating the incision and an outer peripheral edge. A generally hollow stem surrounds the opening and extends outwardly from the base. The stem includes an operative passageway extending along the length of the stem and communicating with the opening in the flexible base. An instrument seal is attached to the stem within the operative passageway for providing a seal around an operative instrument which may be inserted through the instrument seal. An operative valve is attached within the hollow stem for maintaining a gas-tight barrier across the operative passageway. Both the instrument seal and the operative valve are penetrable by the operative instrument.

The hollow stem of the present invention comprises a flexible member defining the operative passageway. By using a flexible stem, the surgical access device allows for increased manipulation of an inserted operable instrument. The hollow stem includes a lower end which is attached to the flexible base and surrounds the opening in the base. The stem extends outwardly away from the base to an upper end. This upper end generally defines the entrance to the operative passageway.

In another aspect of the present invention, the hollow stem comprises a stack of flexible concentric rings made of an elastic material. In this fashion, one of the concentric rings incorporates the instrument seal by comprising a flexible sheet of elastic material extending across the operative passageway within the hollow stem or by having a flexible inner wall defining an operative opening capable of sealing around an inserted surgical instrument.

The instrument seal, which comprises a flexible sheet of elastic material, extends across the operative passageway within the hollow stem to form a centrally disposed opening. This opening allows for insertion of an operative instrument, yet is elastically expandable for sealed contact against the exterior wall of the instrument. In this fashion, various types and sizes of operative instruments may be used.

In another aspect of the present invention, the operative valve comprises a duck-bill valve situated across the operative passageway within the hollow stem. In this fashion, the operative valve is easily manipulated to allow passage of an operative instrument and is self-closing upon removal of the instrument. The duck-bill valve provides a gas-tight barrier across the operative passageway including the ability to retain a gas pressure such as that required to maintain an operative cavity within a patient.

In yet another aspect of the present invention, the surgical access device includes a flexible base having a plurality of flexible hollow stems, each including an instrument seal and an operative valve. Each of the plurality of hollow stems is attached over an opening in the flexible base. In addition, each of these openings isolates a separate surgical incision and provides a separate access path to the operable region within the patient. In this way, a surgeon can access an operable region from a number of locations and positions outside the patient. In addition, each hollow stem may be of a different size or configuration, allowing the use of differing operative instruments.

In yet another aspect of the present invention, the surgical access device includes a hollow stem which extends outwardly from the base at an acute angle. In this way, the invention provides an angled or even oblique access path into the operable region. As previously described, the hollow stem, which is centered over a surgical incision, is flexible and provides for sealing against differing surgical instruments as well as manipulation within the surgical access device itself In another embodiment of the present invention, the surgical access device is provided without an attached hollow stem. In this embodiment, the invention is used to isolate and maintain a superfascial surgical incision in a patient. The invention includes a flexible base which is removably attachable to the skin portion of the patient. The base includes an opening or slit which is placed over and surrounds the surgical incision. A securing device is attached to the base for securing the surgical access device to the patient and for maintaining and isolating the surgical incision. As the securing device is tightened about the patient, the opening in the base as well as the surgical incision are forced open. A flexible stem having a sealed hollow passageway as previously described may be attached to the base over the opening. In this fashion, the surgical access device provides for a sealed access path into an operable region through the incision as previously described.

In yet another embodiment of the present invention, the surgical access device is adapted for maintaining a distended anatomical cavity such as on inflated peritoneum. In this embodiment, the flexible base comprises an elastomeric sleeve for surrounding the distended anatomical cavity. As previously described, the base is removably attached to at least the portion of the skin surrounding the cavity. To enhance the ability of the sleeve base to attach to the portion of skin, an adhesive is typically applied between the portion of the skin and the inner surface of the sleeve. A supporting rib is attached to the base and surrounds at least a portion of the distended cavity. In this fashion, the attached portion of the skin is maintained in the distended position by the rib and attached sleeve base.

A hollow stem is then attached to the elastomeric sleeve base providing an operative passageway in communication with an opening in the base. As previously described, the opening in the base is oriented such that it isolates and surrounds a superfascial surgical incision in the patient adjacent an operative region.

In a method of the present invention, a technique for using a superfascial surgical access device to access an operable region within a patient for the sealed introduction and manipulation of an operative instrument is described. The method includes making a superfascial surgical incision to create an opening within a skin portion of the patient adjacent the desired operative region. A flexible superfascial access device having a flexible planar base and a flexible hollow stem is attached to the patient such that the planar base is sealed against the skin and surrounds the incision. The flexible hollow stem defines an operative passageway which includes an instrument seal and an operative valve for providing sealed communication with the incision through the hollow stem. An operative instrument is then inserted through the operative passageway including the instrument seal and the operative valve and into the operable region of the patient such that the instrument seal maintains a seal around the operative instrument within the stem and allows for sealed manipulation of the instrument within the operable region.

The invention, together with additional features and advantages thereof, which was only summarized in the foregoing passages, will become more apparent to those of skill in the art upon reading the description of the preferred embodiments, which follows in this specification, taken together with the following drawings.

DESCRIPTION OF THE PREFERRED EMBODIMENTS

Figure 1:
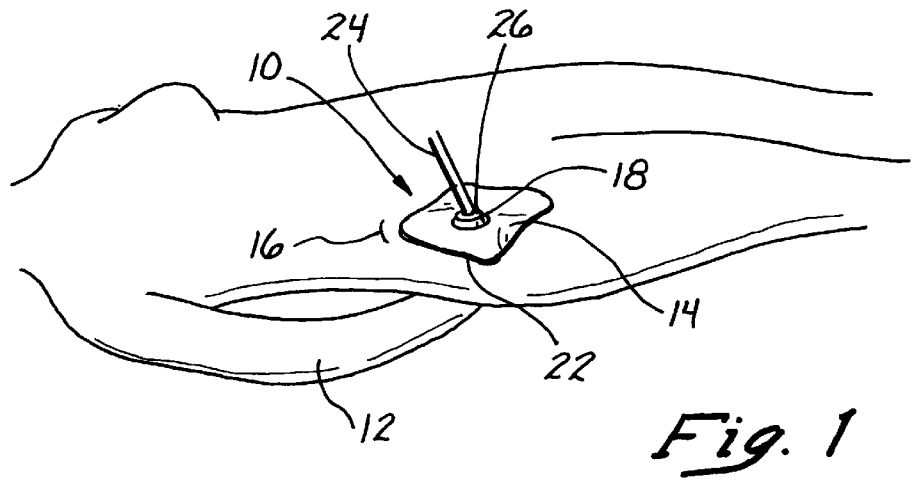
FIG. 1 is a perspective view of an embodiment of a superfascial surgical access device according to the principles of the present invention shown applied to a patient.

FIG. 1 illustrates an embodiment of a surgical access device 10 of the present invention shown applied to a patient 12. The surgical access device 10 has a flexible base 14 for removable attachment to a portion of skin 16 and a hollow stem 18 extending outwardly from the base 14. The flexible base 14 is generally large enough to cover a surgical incision 20 (not seen in FIG. 1) as well as covering sufficient skin 16 to insure adequate adhesion. A peripheral edge 22 surrounds the flexible base 14. An operative instrument 24 is shown passing through an operative passageway 26 in the hollow stem 18.

Figure 2:
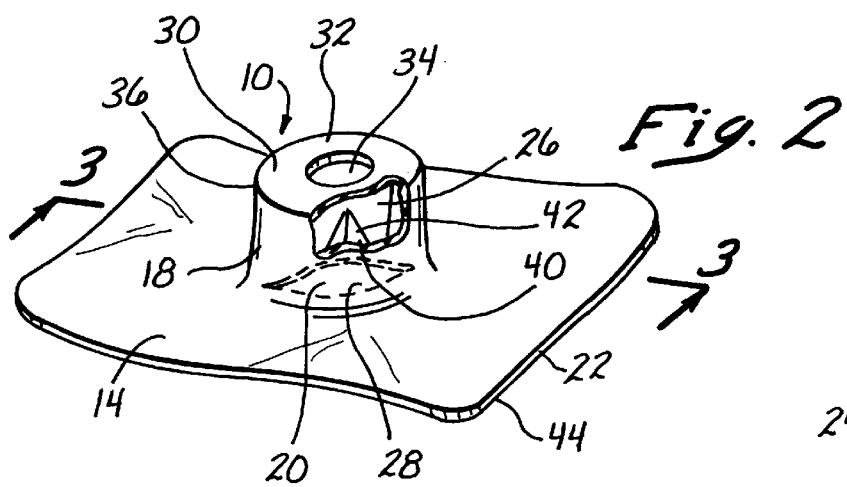
FIG. 2 is a perspective view of the superfascial surgical access device as shown in FIG. 1, including a partial cutaway view to show the instrument seal and operative valve.
Figure 3:
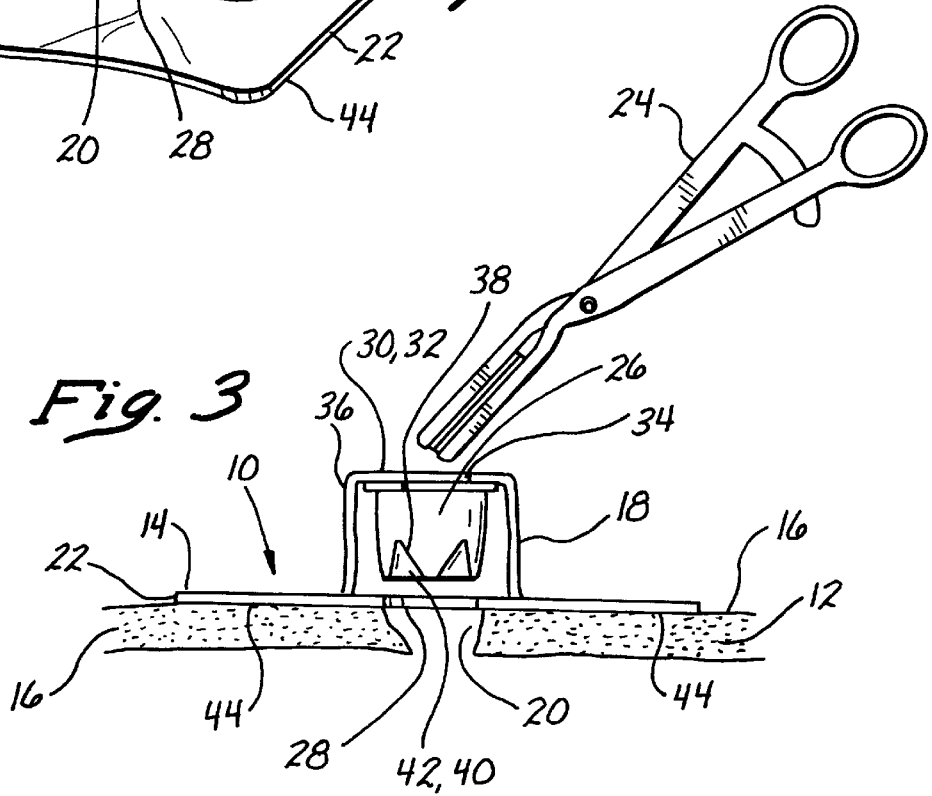
FIG. 3 is a sectional view along section 3—3 of the superfascial surgical access device shown in FIG. 2.

Referring now to FIGS. 2–3, the surgical access device 10 will be described in greater detail. The base 14 is preferably a thin planar sheet of flexible material. The base 14 may be of any shape but preferably is of sufficient surface area to provide secure adhesion to the skin 16 of the patient 12 such that the surgical access device 10 is not moved or removed during the surgical procedure. The peripheral edge 22 provides a transition from the flexible base to the skin 16. In this way the peripheral edge 22 may be smooth and may even taper downwardly towards the skin 16 to prevent the base 14 from being pulled up or otherwise off of the skin 16. The flexible base has an opening 28 for isolating a surgical incision 20. The opening 28 is preferably of the same or a slightly larger size than the incision 20 to provide isolation of the incision 20 as well as for maintaining an incision 20 in an open state. The opening 28 may be cut or otherwise provided in the flexible base 14 prior to attachment to the patient 12 or may be directly made in the flexible base 14 by a surgeon after attachment to the patient 12. In this way, the surgical incision 20 and the opening 28 may be made simultaneously. Typically, this may be done using a surgical blade or other device as is known to those of skill in the art of surgical incisions. The opening 28 is preferably centrally located on the surface of the flexible base 14.

The hollow stem 18 extends outwardly from the flexible base 14 and away from the patient 12. The hollow stem 18 is preferably a flexible member and may be integral with the flexible base 14 such that the two comprise a single molded piece. However, the hollow stem 18 may also be attached to the base using an adhesive or any other method as is known in the art of joining surgical elastic materials. The hollow stem 18 is centered over the opening 28 such that the operative passageway 26 provides a direct path to the incision 20. By being flexible, the hollow stem 18 allows for increased maneuverability of an operative device or instrument 24 passing through the operative passageway 26.

An instrument seal 30 is attached across the hollow stem 18. In this way, a seal is created around an operative instrument 24 inserted through the hollow stem 18. In a preferred embodiment, the instrument seal 30 comprises a flexible sheet of elastic material 32 extending across the hollow stem 18 to form a centrally disposed opening 34. This opening 34 is elastically expandable for sealed contact against the exterior walls of an inserted instrument 24. A highly elastic material is desirable since this minimizes the necessity to provide different instrument seals 30 having different disposed opening diameters 34. The flexible sheet of elastic material 32 preferably extends across an upper end 36 of the hollow stem 18. This allows for the flexible base 14, the hollow stem 18 and the instrument seal 30 to all be made from a single integral piece. However, the instrument seal 30 may be attached most anywhere across the hollow stem 18. An adhesive or any other method as is known in the art, may be used to attach the instrument seal 30 to the inner walls of the operative passageway 26.

An operative valve 38 may also be attached within said hollow stem 18. The operative valve 38 provides a penetrable seal across the operative passageway 26 within the hollow stem 18 and may also be used to maintain an inflated or distended peritoneum. In this fashion, the instrument seal 30 is preferably placed outwardly from the flexible base 14 in relation to the operative valve 38 such that an operative instrument 24 inserted into the hollow stem 18 is sealed across the instrument seal 30 prior to penetrating the gas-tight barrier of the operative valve 38.

The operative valve 38 may be attached to the interior wall of the hollow stem 18 and extend across the operative passageway 26. However, the operative valve 38 may also be attached to or an integral part of the flexible base 14.

Attachment of the operative valve 38 is similar to that described for the instrument seal 30. A plurality of flexible flaps 40 allow penetration through the valve 38 while maintaining a gas-tight barrier when not penetrated. In a preferred embodiment, the operative valve 38 may be a duck-bill valve 42 such as the duck-bill valve described in U.S. Pat. No. 5,443,452, to Hart et al., is incorporated herein fully by reference. However, any type of valve or seal which is penetrable by an operative instrument 24 and which can maintain a gas-tight barrier across the operative passageway 26 within the hollow stem 18 may be utilized.

An adhesive coating 44 may be applied to the flexible base 14 or the skin 16 surrounding the surgical incision 20 to positively secure the surgical access device 10 the patient 12. The adhesive 44 may be formed of any suitable non-tissue reactive adhesive material such as, for example, Hollister Medical Adhesive, manufactured by Hollister, Inc., or Elastoplast, manufactured by Biersdorf, Inc. A release sheet (not shown) may be supplied when the adhesive coating 44 is applied to the flexible base 14 prior to attachment to the skin 16. The release sheet may be formed of any suitable paper or plastic material allowing the release sheet to be manually pealed away from the layer to expose the adhesive coating 44. In addition to an adhesive coating 44, the surgical access device 10 may also be attached to a patient 12 in other ways. For example, the natural adhesion of the material, securing straps and devices or any other method of attaching a flexible sheet of material to the skin. The use of securing straps advantageously allows the flexible base to be tightened against the skin, maintaining an open incision 20.

Figure 4:
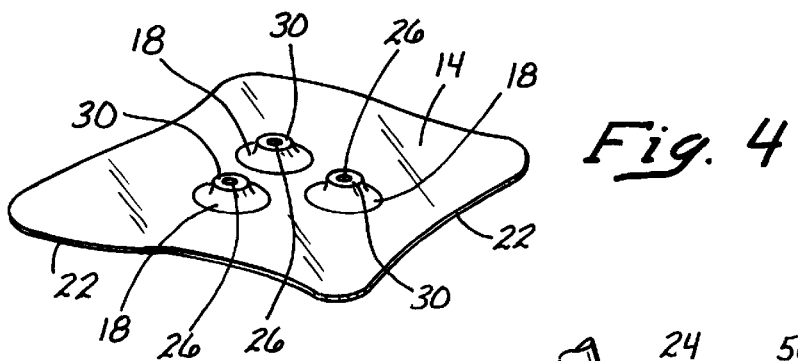
FIG. 4 is a perspective view of the superfascial surgical access device shown in FIG. 1 including multiple hollow stems and operative passageways.

FIG. 4 shows the surgical access device 10 having a plurality of hollow stems 18 attached to the base 14. In this fashion, the surgical access device 10 provides access into an operative region (not shown) through almost any number of differing locations. The use of multiple access devices 10 also allows the use of multiple surgical or other operable instruments 24 each of which may be passed through an individual operative passageway 26 within each hollow stem 18. In addition, each of the hollow stems 18 may be provided with differing size and types of instrument seals 30 and/or operative valves 38. The flexible base 14 may also be used to support various sizes of openings 28 to be covered by the hollow stems 18. This greatly increases the flexibility of the surgical procedures available within the operative region.

Figure 5:
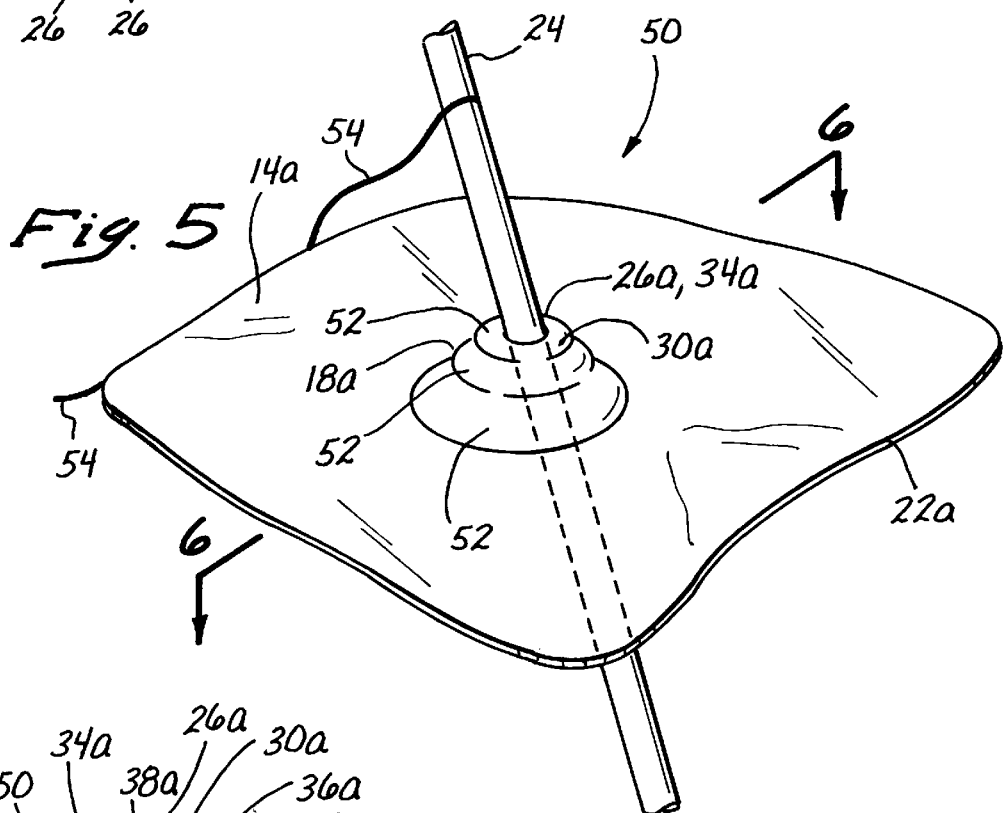
FIG. 5 is a perspective view of a superfascial surgical access device according to an alternate embodiment of the present invention.
Figure 6:
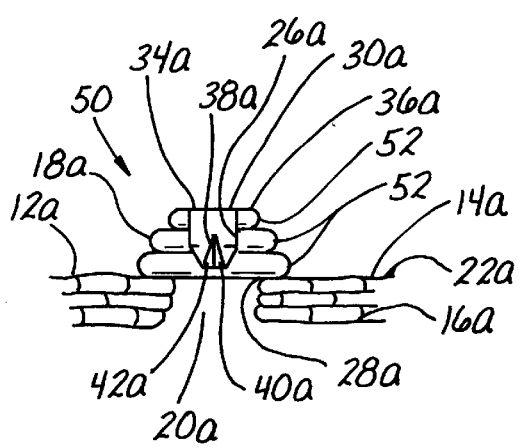
FIG. 6 is a sectional view along section 6—6 of the superfascial surgical access device shown in FIG. 5.
Figure 7:
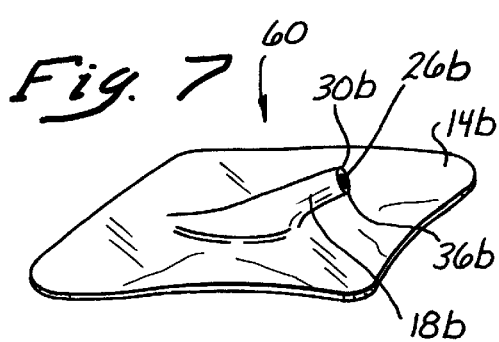
FIG. 7 is a perspective view of a superfascial surgical access device according to an embodiment of the present invention showing an angled operative passageway.
Figure 8:
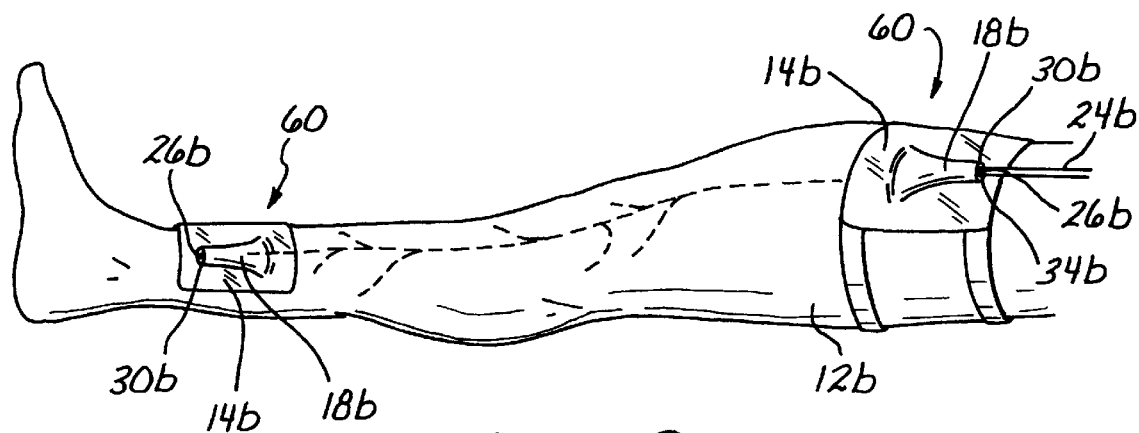
FIG. 8 is a perspective view of a pair of superfascial surgical access devices as shown in FIG. 7 applied to a patient.
Figure 9:
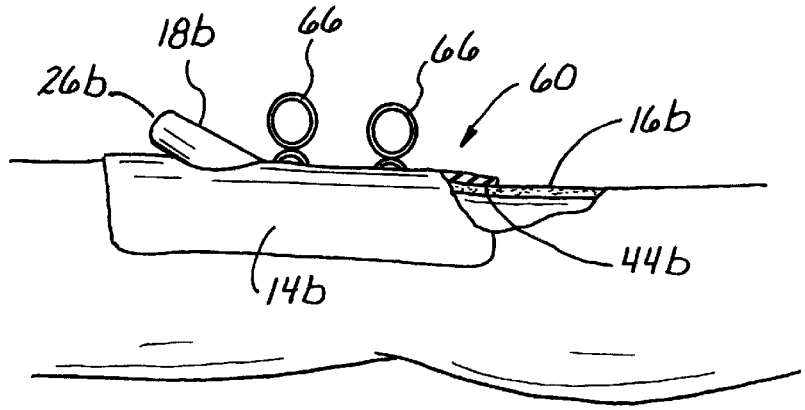
FIG. 9 is a perspective view of the superfascial surgical access device of FIG. 7 shown applied to a patient and including a pair of lifting rings.
Figure 10:
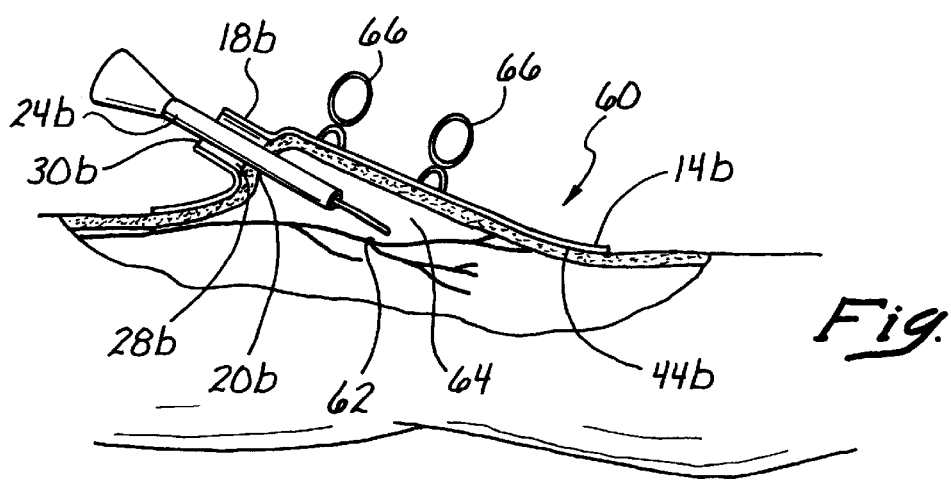
FIG. 10 is a perspective view of the superfascial surgical access device of FIG. 9 shown applied to a patient and lifted upwardly to create an operable cavity.

Referring now to FIGS. 5–6, an alternative embodiment of a surgical access device 50 constructed in accordance with the principles of the present invention will be described. In this embodiment, like features to those of the previous embodiment are designated by like reference numerals, succeeded by the letter "a". The surgical access device 50 includes a flexible base 14*a* having a peripheral edge 22*a* as described in the previous embodiment. However, in this embodiment, the hollow stem 18*a* comprises a plurality of flexible concentric rings 52 made from an elastic material. These flexible rings 52 may be hollow concentric tubes which are stacked on top of each other. However, the rings 52 may also be made from folds of material. The flexible rings 52 may be made of any cross-sectional shape such as circular, oval or any other shape which facilitates access for various surgical instruments 24*a* within the patient 12*a*.

The instrument seal 30*a* may be made from one of the concentric rings 52 of elastic material. In this fashion, the instrument seal 30*a* is a flexible ring 52 having a flexible sheet of elastic material 32*a* extending across the operative passageway 26*a* as previously described. However, the instrument seal 30*a* may also be comprised of a flexible ring 52 which extends inwardly to form a smaller diameter than the remaining concentric rings 52. Thus, the instrument seal 30*a* which is preferably an elastic material, is expandable such that it surrounds an inserted operative instrument 24*a* to provide the desired seal. This seal is made as the inner diameter of the seal 30*a* forms a continuous contact against the exterior wall of the instrument 24*a*. An operative valve 38*a* may be disposed across the operative passageway 26*a* to provide a gas-tight barrier as previously described.

Referring now to FIGS. 7–10, a second alternative embodiment of a surgical access device constructed in accordance with the principles of the invention will be described. In this embodiment, like features to those of previous embodiments are designated by like reference numerals, succeeded by the letter "b". The surgical access device 60 includes a flexible base 14*b* and a hollow stem 18*b* which is oriented at an angle. This embodiment allows for an angled access which may be an oblique entrance into an operable region 62 which may otherwise be impossible. In particular, a surgical procedure, such as a vein harvesting procedure, requires a relatively shallow access adjacent the surgical incision 20*b*. This type of procedure is generally not possible utilizing a trocar which prevents the angled access. The hollow stem 18*b* may be provided at any angle which orients up from the flexible base 14*b*. However, an angle of between approximately 20 degrees and 60 degrees is found preferable.

When performing a procedure, such as a vein harvesting procedure within the leg of a patient 12*b*, it is often necessary to create an anatomical cavity 64 within the operative region 62 without the use of insufflation. To create this anatomical cavity 64, the surgical access device 60 is first attached to a portion of skin 16*b* using an adhesive coating 44*b*. A pull tab 66 attached to the flexible base 14*b* is used to pull the flexible base outwardly away from the patient 12*b*. In this way, the skin 16*b* attached to the flexible base 14*b* is pulled away, exposing an operative region 62 and creating an anatomical cavity 64. Any number of pull tabs 66 or other devices which allow the surgical access device 60 to be drawn outwardly away from the patient 12*b* may be utilized. The pull tabs 66 may be of a size or shape that facilitates a strong grip with a gloved hand. The pull tabs 66 may even comprise hoops or rings made from a plastic or metal.

Figure 11:
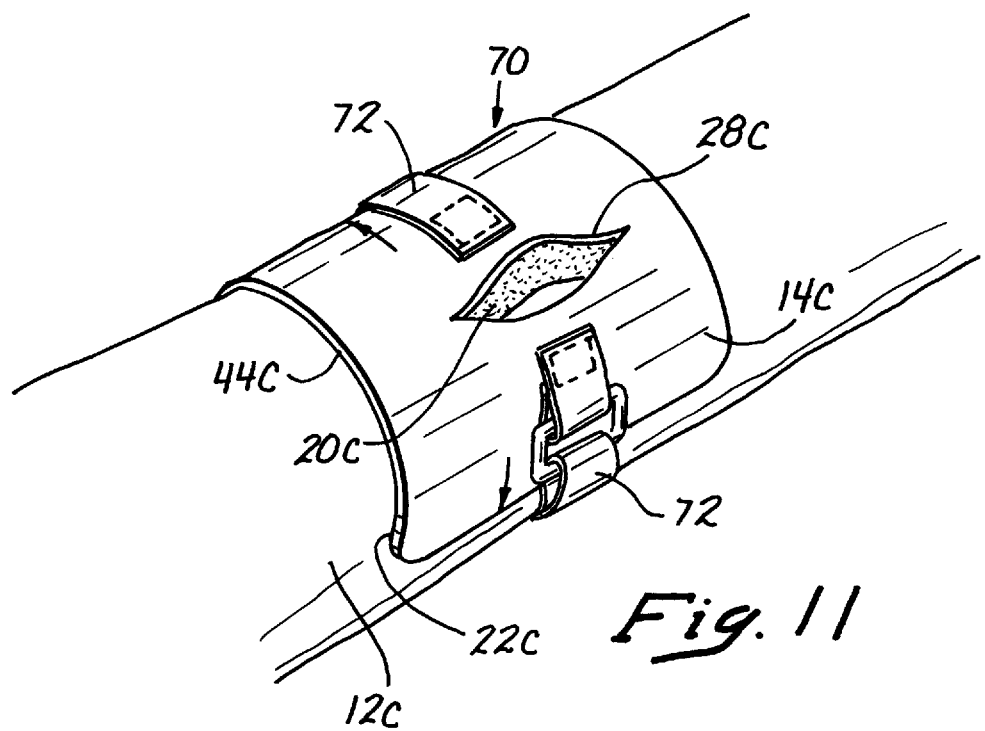
FIG. 11 is a perspective view of a superfascial surgical access device according to an embodiment of the present invention shown maintaining an open incision on a patient.

FIG. 11 illustrates a third alternative embodiment of a surgical access device constructed in accordance to the principles of the present invention. In this embodiment, like features to those embodiments are designated by like reference numerals succeeded by the letter "c". The surgical access device 70 includes a flexible base 14c having a centrally located opening 28c for isolating a superfascial incision 20c within a portion of skin 16c of a patient 12c. An adhesive coating 44c may be applied between the flexible base 14c and the skin 16c to insure adequate attachment of the access device 70 to the patient 12c. However, alternative securing devices 72 may be used alone or in conjunction with the adhesive coating 44c. The securing device 72 may include a rigid or flexible strap which extends around the patient 12c securing the surgical access device 70 to the skin 16c. However, any form of securing device 72 such as bands, hooks or any other device for securing a flexible planar base 14c to the patient 12c may be utilized. By cinching down on the securing device 72, the planar base 14c is advantageously stretched. In this fashion, the opening in the base 14c is forced open as is the isolated incision 20c. Thus, the incision 20c may be maintained open during a surgical procedure.

The surgical access device 70 is also advantageously designed such that the opening 28c may be made simultaneously with the surgical incision 20c. In this fashion, the surgical access device 70 is secured to the skin 16c and the opening 28c along with the surgical incision 20c are made together. The securing device 72 may then be cinched somewhat tighter to maintain both the opening 28c and the surgical incision 20c open. A removable hollow stem 18c, having an instrument seal 30c and an operative valve 38c may be attached to the surgical access device 70 such that an operative passageway 26c is provided through the hollows stem 18c and into the surgical incision 20c. By providing a removable hollow stem 18c, both laparoscopic and open surgical techniques can be utilized during a single surgical procedure and utilizing a single surgical incision 20c.

Figure 12:
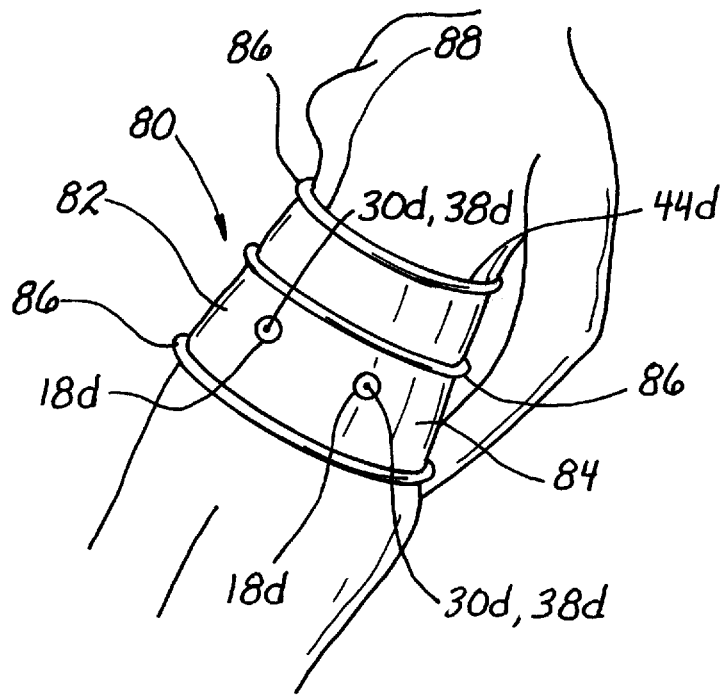
FIG. 12 is a perspective view of a superfascial surgical access device according to an embodiment of the present invention shown maintaining an anatomical cavity of a patient.

FIG. 12 shows a fourth alternative embodiment of a surgical access device constructed in accordance with the principles of the present invention. In this embodiment, like features to those of previous embodiments are designated by like reference numerals succeeded by the letter "d". The surgical access device 80 includes an elastomeric sleeve 82 for surrounding a distended anatomical cavity 84. Typically, the distended cavity will be an abdominal cavity, but the principles also apply to other regions such as a leg. A rib is attached to the sleeve 82, such that it surrounds the distended anatomical cavity 84 while supporting the shape of the distended attached sleeve 82.

The surgical access device 80 is used to maintain a distended anatomical cavity 84 by first securing the sleeve 82 to at least a portion of skin 88 surrounded by the sleeve 82. An adhesive coating 44d may preferably be utilized since the skin 88 must remain attached to the sleeve 82. Prior to securing the sleeve 82 to the skin 88, the anatomical cavity 84 is preferably fully distended. This may be accomplished by insufflating the cavity 84 using a positive pressure as is known to those of skill in the art. Alternatively, the sleeve 82 may be adhered to the skin 88 without first distending the cavity and the sleeve pulled outwardly as previously described. A rib 86 is then secured to the sleeve 82 to support and maintain the sleeve 82 in the distended position. In this way, the skin 88 surround the distended anatomical cavity 84 is secured to the sleeve 82 which is structurally supported by the rib 86. Additional ribs or other structurally supporting members 86 may be attached to the sleeve 82 to further support and maintain the distended anatomical cavity 84.

Access within the anatomical cavity 84 may be accomplished by attaching a hollow stem 18d, including an instrument seal 30d and an operative valve 38d as previously described. A surgical incision 20d may be made prior to securing the surgical access device 80 to the patient 12d. Alternatively, an incision may be made through both the sleeve 82 and the patient 12 in a similar fashion to that described with the base 14. In this fashion, the surgical access device 80 acts to maintain the distended anatomical cavity 84 as well as providing superfascial access at any desired location along the sleeve 82. In addition, insufflation may be used to maintain the distended anatomical cavity 84. The sleeve 82 which is preferably a sheet of elastomeric material may be provided as a continuous sleeve or alternative as a single sheet which is wrapped around the anatomical cavity 84 and secured to itself.

While this invention has been described with respect of various specific examples and embodiments, it is to be understood that the invention is not limited thereto and that it can be variously practiced within the scope of the following claims.

What is claimed is:

1. A surgical access device for isolating a superfascial incision and for providing a sealed access path for a surgical instrument into an operable region in communication with the incision, comprising:

a flexible base for removable attachment to a portion of skin surrounding the incision, said base having an opening for isolating the incision and an outer peripheral edge;

a generally hollow stem extending outwardly from said base, said stem having an operative passageway in communication with said opening;

an instrument seal attached to said stem within said operative passageway;

an operative valve attached to said stem within said operative passageway and having properties for inhibiting gas flow in response to positive gas pressures within the operable region; and wherein said instrument seal provides a gas seal around the operative instrument when the operative instrument is inserted into the stem.

2. The surgical access device as recited in claim 1 wherein said instrument seal comprises a flexible sheet of elastic material extending across said hollow stem and including portions defining a centrally disposed opening sized and configured for insertion of said operative instrument, and wherein said portions are elastically expandable to facilitate sealing engagement of said inserted instrument by said seal.

3. A surgical access device for isolating a superfascial incision and for providing a sealed access path into an operable region in communication with the incision, comprising;

a flexible base for removable attachment to a portion of skin surrounding the incision, said base having an opening for isolating the incision and an outer peripheral edge;

a generally hollow stem extending outwardly from said base, said stem having an operative passageway in communication with said opening;

an instrument seal attached to said stem within said operative passageway;

a flexible sheet of elastic material included in the instrument seal and extending across said hollow stem, the sheet including portions defining a centrally-disposed opening sized and configured for insertion of an operative instrument, said portions being elastically expandable to facilitate sealing engagement of the operative instrument by said instrument seal;

an operative valve attached to said stem within said operative passageway for maintaining a gas-tight barrier;

wherein said instrument seal provides a seal around the operative instrument when the operative instrument is inserted into the stem, and said operative valve provides a penetrable opening in the seal across said operative passageway; and wherein said hollow stem has an upper end and said instrument seal extends across said upper end.

4. The surgical access device as recited in claim 1 wherein said hollow stem comprises a stack of flexible concentric rings made from an elastic material.

5. The surgical access device as recited in claim 4 wherein at least one of said stack of concentric rings is said instrument seal.

6. The surgical access device of claim 4 wherein said instrument seal comprises at least one flexible ring of elastic material extending across said hollow stem to form a centrally disposed opening for insertion of said operative instrument and wherein said centrally disposed opening is expandable for sealed contact against said inserted instrument.

7. A surgical access device for isolating a superfascial incision and for providing a sealed access path into an operable region in communication with the incision, comprising:

a flexible base for removable attachment to a portion of skin surrounding the incision, said base having an opening for isolating the incision and an outer peripheral edge;

a generally hollow stem extending outwardly from said base, said stem having an operative passageway in communication with said opening;

an instrument seal attached to said stem within said operative passageway;

an operative valve, including a duck-bill valve, attached to said stem within said operative passageway for maintaining a gas tight barrier; and wherein said instrument seal provides a seal around an operative instrument inserted through said instrument seal and said operative valve provides a penetrable opening and seal across said operative passageway.

8. The surgical access device of claim 1 wherein said base further comprises a second opening for isolating a second superfascial incision in said patient and a second generally hollow stem extending outwardly from said second opening, said second stem including a second instrument seal and a second operative valve.

9. The surgical access device recited in claim 1 wherein the operative valve is disposed between the instrument seal and the base.

10. The surgical access device recited in claim 1 wherein the surgical instrument is operable from a location exterior of the access device.

11. The surgical access device recited in claim 1, wherein:

the instrument seal has properties for forming a seal inhibiting gas flow through the stem when the surgical instrument is operatively disposed in the access device; and the operative valve has properties for forming a seal inhibiting gas flow through the stem when the surgical instrument is removed from the access device.

12. The surgical access device recited in claim 1 wherein the operative region is an abdominal cavity and the superfascial incision is in an abdominal wall.

13. The surgical access device recited in claim 1, wherein:

the flexible base has the general configuration of a plane; and the stem has an axis disposed at other than a normal angle to the plane of the base.

14. The surgical access device recited in claim 13 wherein the angle between the axis of the stem and the plane of the base is in a range between 20° and 60°.

* * * * *